United States Patent
Somma et al.

(10) Patent No.: US 8,979,005 B2
(45) Date of Patent: Mar. 17, 2015

(54) PROCESS FOR RECYCLING ABSORBENT SANITARY PRODUCTS

(71) Applicant: Fater S.p.A., Pescara (IT)

(72) Inventors: Marcello Somma, Pescara (IT); Giorgio Vaccaro, Pescara (IT); Jan K. Michalek, Pataskala, OH (US); Theodore Thomas, Columbus, OH (US)

(73) Assignee: Fater S.p.A., Pescara (IT)

( * ) Notice: Subject to any disclaimer, the term of this patent is extended or adjusted under 35 U.S.C. 154(b) by 185 days.

(21) Appl. No.: 13/686,812

(22) Filed: Nov. 27, 2012

(65) Prior Publication Data

US 2013/0146689 A1 Jun. 13, 2013

(30) Foreign Application Priority Data

Nov. 28, 2011 (IT) .............................. TO2011A1090

(51) Int. Cl.
| | |
|---|---|
| *B02C 17/18* | (2006.01) |
| *B02C 23/00* | (2006.01) |
| *A61L 2/07* | (2006.01) |
| *A61L 11/00* | (2006.01) |
| *B09B 3/00* | (2006.01) |

(52) U.S. Cl.
CPC . *B02C 23/00* (2013.01); *A61L 2/07* (2013.01); *A61L 11/00* (2013.01); *B09B 3/0083* (2013.01)
USPC ................................ 241/23; 241/65; 241/299

(58) Field of Classification Search
CPC .............................. B02C 19/06; B02C 19/186
USPC ............................................. 241/23, 65, 299
See application file for complete search history.

(56) References Cited

U.S. PATENT DOCUMENTS

| | | | |
|---|---|---|---|
| 3,981,855 A | * | 9/1976 | Klein .............................. 526/63 |
| 4,050,897 A | * | 9/1977 | Klein ............................ 422/205 |
| 4,303,501 A | | 12/1981 | Steffens |
| 4,970,267 A | | 11/1990 | Bailey et al. |
| 5,292,075 A | | 3/1994 | Bartlett |
| 5,361,994 A | | 11/1994 | Holloway |

(Continued)

FOREIGN PATENT DOCUMENTS

| | | |
|---|---|---|
| DE | 4133699 A1 | 4/1993 |
| DE | 19631442 A1 | 2/1998 |

(Continued)

OTHER PUBLICATIONS

Italian search report for application No. TO20111090 dated Mar. 28, 2012.

(Continued)

*Primary Examiner* — Faye Francis
*Assistant Examiner* — Onekki Jolly
(74) *Attorney, Agent, or Firm* — Patterson & Sheridan, LLP

(57) ABSTRACT

A process for treating used absorbent sanitary products by providing a rotary cylindrical autoclave having an inner surface and two ends, at least one of which terminates in a hatch that can be opened to enable access to the autoclave and sealably closed to enable pressurization of the autoclave; loading the autoclave with closed absorbent sanitary products; heating to a sterilization temperature and pressurizing the autoclave and at the same time driving the autoclave in rotation about a longitudinal axis thereof; and providing inside the autoclave a load of high-density tearing elements designed to facilitate thermal and physical destructuring of the absorbent sanitary products.

6 Claims, 2 Drawing Sheets

(56) References Cited

U.S. PATENT DOCUMENTS

| | | | |
|---|---|---|---|
| 5,429,311 A | 7/1995 | Cina et al. | |
| 5,558,745 A | 9/1996 | Conway et al. | |
| 5,618,003 A | 4/1997 | Akiyoshi et al. | |
| 5,655,718 A * | 8/1997 | Anderson | 241/17 |
| 5,799,883 A | 9/1998 | Lewis et al. | |
| 6,200,715 B1 | 3/2001 | Fuller et al. | |
| 6,238,516 B1 | 5/2001 | Watson et al. | |
| 6,726,136 B2 * | 4/2004 | Swisher et al. | 241/65 |
| 6,752,337 B2 * | 6/2004 | Koenig | 241/23 |
| 7,407,912 B2 | 8/2008 | Mertens et al. | |
| 2003/0129915 A1 | 7/2003 | Harriz | |
| 2005/0155491 A1 | 7/2005 | Faust et al. | |
| 2007/0135563 A1 | 6/2007 | Simmons et al. | |
| 2007/0142532 A1 | 6/2007 | Lee | |
| 2008/0217444 A1 * | 9/2008 | Michalek et al. | 241/1 |
| 2009/0032626 A1 | 2/2009 | Armstrong et al. | |
| 2010/0093949 A1 | 4/2010 | Herfert et al. | |
| 2010/0292401 A1 | 11/2010 | Grimes | |

FOREIGN PATENT DOCUMENTS

| | | |
|---|---|---|
| DE | 19749039 A1 | 7/1999 |
| DE | 19821473 A1 | 11/1999 |
| EP | 0739657 A1 | 10/1996 |
| EP | 0983803 A1 | 3/2000 |
| GB | 1224344 A | 3/1971 |
| JP | 2000229250 A | 8/2000 |
| JP | 2004113915 A | 4/2004 |
| JP | 4056839 B2 | 3/2008 |
| JP | 4685973 B1 | 5/2011 |
| WO | 9207995 A1 | 5/1992 |
| WO | 9420668 A1 | 9/1994 |
| WO | 9524967 A1 | 9/1995 |
| WO | 9627045 A1 | 9/1996 |
| WO | 2006015423 A1 | 2/2006 |
| WO | 2010065088 A1 | 6/2010 |

OTHER PUBLICATIONS

Zohuriaan-Mehr et al., Superabsorbent Polymer Materials: A Review, Iranian Polymer Journal, 2008, 17(6), pp. 451-477.

* cited by examiner

PROCESS FOR RECYCLING ABSORBENT SANITARY PRODUCTS

CROSS-REFERENCE TO RELATED APPLICATIONS

This application claims benefit of Italian Patent Application No. TO2011A001090, filed Nov. 28, 2011, which is herein incorporated by reference.

BACKGROUND OF THE INVENTION

1. Field of the Invention

The present invention relates to a process for recycling used absorbent sanitary products.

By the term "absorbent sanitary products" is meant in general disposable absorbent products, such as: baby diapers, incontinence absorbent pads, ladies sanitary pads, bed mats, etc.

2. Description of the Related Art

Absorbent sanitary products are generally made up of a wide range of different materials, amongst which sheets of plastic material, cellulose fluff, superabsorbent polymers, sheets of non-woven fabric, etc.

Absorbent sanitary products contain high-quality materials such as plastic and cellulose, and it would be desirable to recover said materials to use them in a new production cycle or else for the production of energy.

Currently, used absorbent sanitary products are disposed of as undifferentiated waste to be sent to rubbish dumps. The component materials of used absorbent sanitary products are not recovered in the first place because the various materials (cellulose fibres, superabsorbent polymers, sheets of plastic material, etc.) are intimately interconnected, and to obtain separation of the materials it would be necessary to carry out a complete destructuring of the products. In addition, used absorbent sanitary products contain organic excretions and bacteria, and it would be necessary to carry out a sterilization of the products prior to recycling of the materials.

For the above reasons, used absorbent sanitary products are not included amongst recyclable waste products for which differentiated collection is carried out.

It is estimated that absorbent sanitary products constitute approximately 2-3% of the total of urban solid waste. However, where a differentiated collection is carried out with a high percentage of differentiation of the waste (with a percentage of differentiated waste higher than 60% of the total) the percentage of absorbent sanitary products with respect to the remaining part constituted by the undifferentiated residual fraction rises to approximately 20%.

The high percentage of absorbent sanitary products with respect to the residual fraction of non-recyclable waste renders highly desirable the availability of equipment and processes that enable a treatment of absorbent sanitary products to be carried out aimed at recycling their component materials in an efficient and economically convenient way.

Currently known techniques for treatment of used absorbent sanitary products are not satisfactory. A first known technique envisages carrying out washing of the used absorbent products with water, alkalis, and soap and separating the cellulose from the plastic during the washing operation. Examples of this technique are disclosed in the documents Nos. WO 94/20668 and WO 96/27045.

The document No. U.S. Pat. No. 5,292,075 describes a process in which the dirty absorbent sanitary products are preliminarily shredded. The shredded material is then washed in a washing machine comprising a perforated cylindrical drum that withholds the plastic material inside it. The material containing the cellulose pulp is then dehydrated.

These techniques of treatment of absorbent sanitary products are in actual practice problematical to implement since the washing water would contain a high amount of pollutants, such as gelified superabsorbent polymers and organic residue, which renders problematical disposal thereof. Drying of the cellulose after washing moreover entails a high expenditure of energy.

A further difficulty derives from the fact that used absorbent sanitary products are normally thrown away folded and closed to form a pack, with the outer plastic layer of the products that forms an impermeable barrier. If the products are treated in the form in which they have been thrown away, the outer impermeable layer prevents an effective sterilization of the products. On the other hand, a preliminary treatment as described in U.S. Pat. No. 5,292,075 entails the need to shred articles with a high content of organic excretions, bacteria, and contaminants.

The document No. JP 2004113915 describes a process for treating diapers that contain absorbent polymers, whereby the used diapers are set in a pressurized closed vessel together with sawdust. Inside the vessel the diapers are treated with steam at high temperature and high pressure for a pre-set time. Steam treatment is carried out at a pressure of 15-25 atm and at a temperature of 150-250° C. This document envisages use of the absorbent sanitary products, after said treatment, as fertilizers following upon fermentation.

The document No. WO 2010/065088 describes an autoclave for the treatment of urban solid waste that envisages drying of the waste using steam. The apparatus described in the document WO 2010/065088 comprises a rotary cylindrical autoclave provided with at least one hatch that can be opened to enable access to the autoclave and sealably closed to enable pressurization of the autoclave, an inlet for contact steam that comes into direct contact with the waste contained inside the autoclave, a plurality of straight hollow blades, which are designed to conduct non-contact steam, project from the inner surface of the autoclave, and are supplied with non-contact steam. This apparatus enables sterilization of urban solid waste and drying of the waste during treatment in the autoclave. The apparatus described in the document WO 2010/065088 has been developed for treatment of undifferentiated urban solid waste and does not contains specific teachings to obtain sterilization, drying, and separation of the component materials of absorbent sanitary products.

SUMMARY OF THE INVENTION

The object of the present invention is to provide a process for treating used absorbent sanitary products that will enable sterilization, drying, and destructuring of used absorbent sanitary products in order to carry out recovery of the constituent materials.

According to the present invention, the above object is achieved by a process having the characteristics forming the subject of Claims 1.

The claims form an integral part of the teaching provided herein in relation to the invention.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be

DETAILED DESCRIPTION

Figure 1:
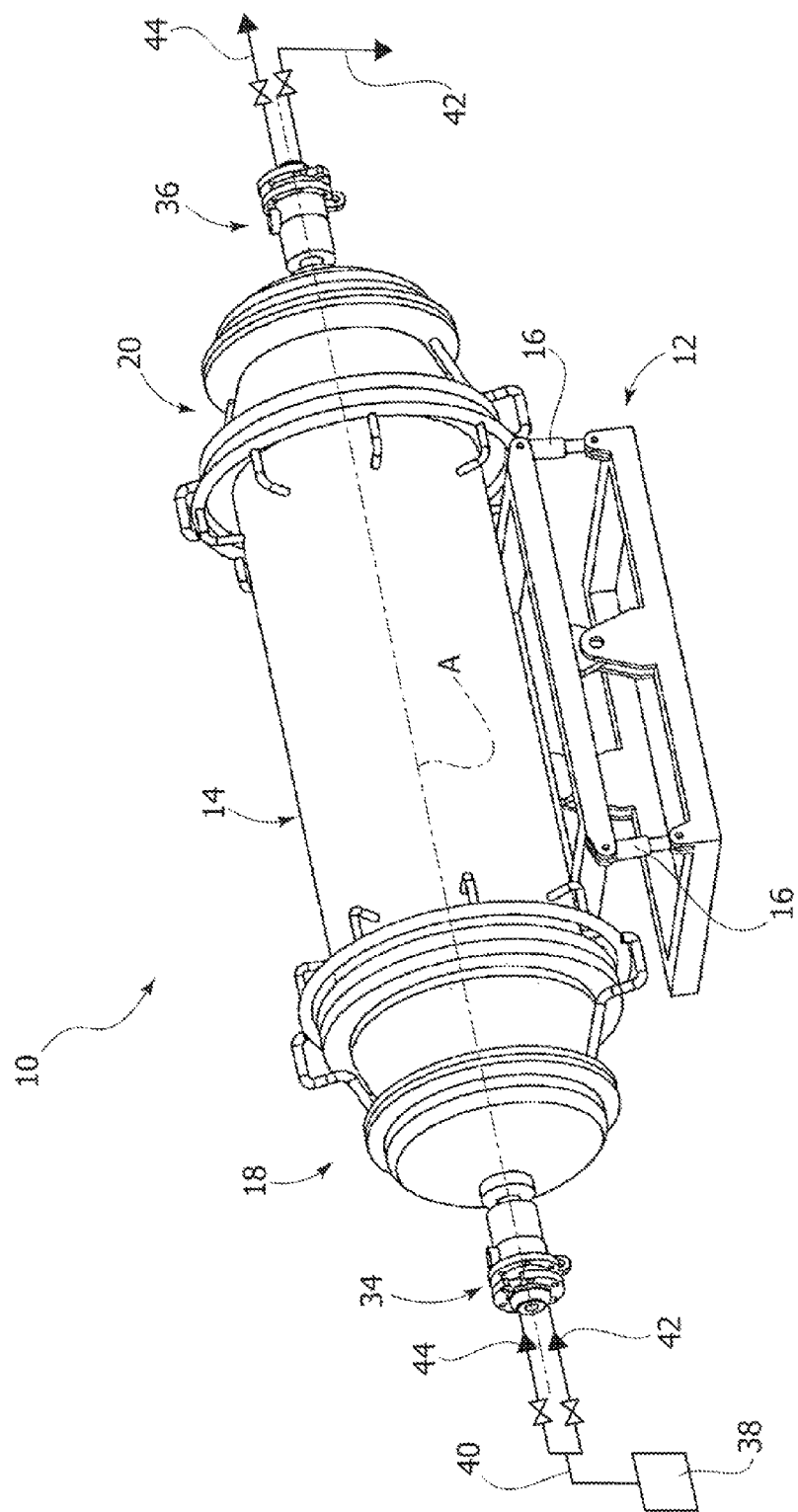
FIG. 1 is a perspective view of a rotary-autoclave apparatus for treating waste.

With reference to FIG. 1, designated by 10 is a rotary-autoclave apparatus for treating used absorbent sanitary products. The apparatus 10 comprises a stationary structure 12, which carries a cylindrical autoclave 14 that turns about its longitudinal axis A. The apparatus 10 comprises a driving device (not illustrated), which drives the autoclave 14 in rotation about the axis A. The supporting structure 12 may be provided with actuators 16 for varying the inclination of the autoclave 14 with respect to a horizontal axis, which enables tilting of the autoclave 14 between a loading/unloading position and a working position. The autoclave 14 has two ends, at least one of which terminates in a hatch that can be opened to enable access to the internal space of the autoclave and sealably closed to enable pressurization of the internal space. In the example illustrated two openable hatches 18, 20 are provided, which can be used, for example, for loading the autoclave with the products to be treated and for unloading the treated products. Alternatively, a single openable hatch could be provided, which can be used both for loading and for unloading.

The apparatus 10 comprises a circuit for heating and pressurizing the autoclave 14 in order to heat the absorbent sanitary products to a sterilization temperature.

The hatches 18, 20 are provided with respective rotary connectors 34, 36 for inlet and outlet of heating steam coming from a steam generator 38. The flow of heating steam can be divided into a flow of non-contact steam 42 that traverses ducts located on the inner wall of the autoclave 14 and a flow of contact steam 44 that comes into direct contact with the products to be treated and pressurizes the internal volume of the autoclave 14. On the outlet connector 36 the flow of non-contact steam 42 and the flow of contact steam 44 are divided and treated separately, for example as described in the document No. WO 2010/065088.

Typically, absorbent sanitary products comprise an absorbent core of cellulose fibres and of superabsorbent polymers. The absorbent core is usually enclosed between two sheets of plastic material joined together. Typically, the backsheet is impermeable, whereas the topsheet is porous. Used absorbent sanitary products are normally folded up so as to enclose the product in the form of a pack within the impermeable backsheet. Usually adhesive tabs are provided for closing the folded product. The organic excretions are thus enclosed within a sealed sheet of impermeable plastic material.

The present invention envisages carrying out the treatment of absorbent sanitary products just as they are collected, i.e., in the form where they are closed to form a pack, and without any preliminary treatment for opening the products.

To obtain an effective action of drying and sterilization during treatment in the autoclave 14 it is necessary to obtain destructuring of the products so as to expose all the organic substances to the sterilization temperature in every point inside the autoclave 14. Destructuring of the absorbent sanitary products is absolutely essential to achieve a complete sterilization and to separate the plastic from the cellulose fibres.

Figure 2:
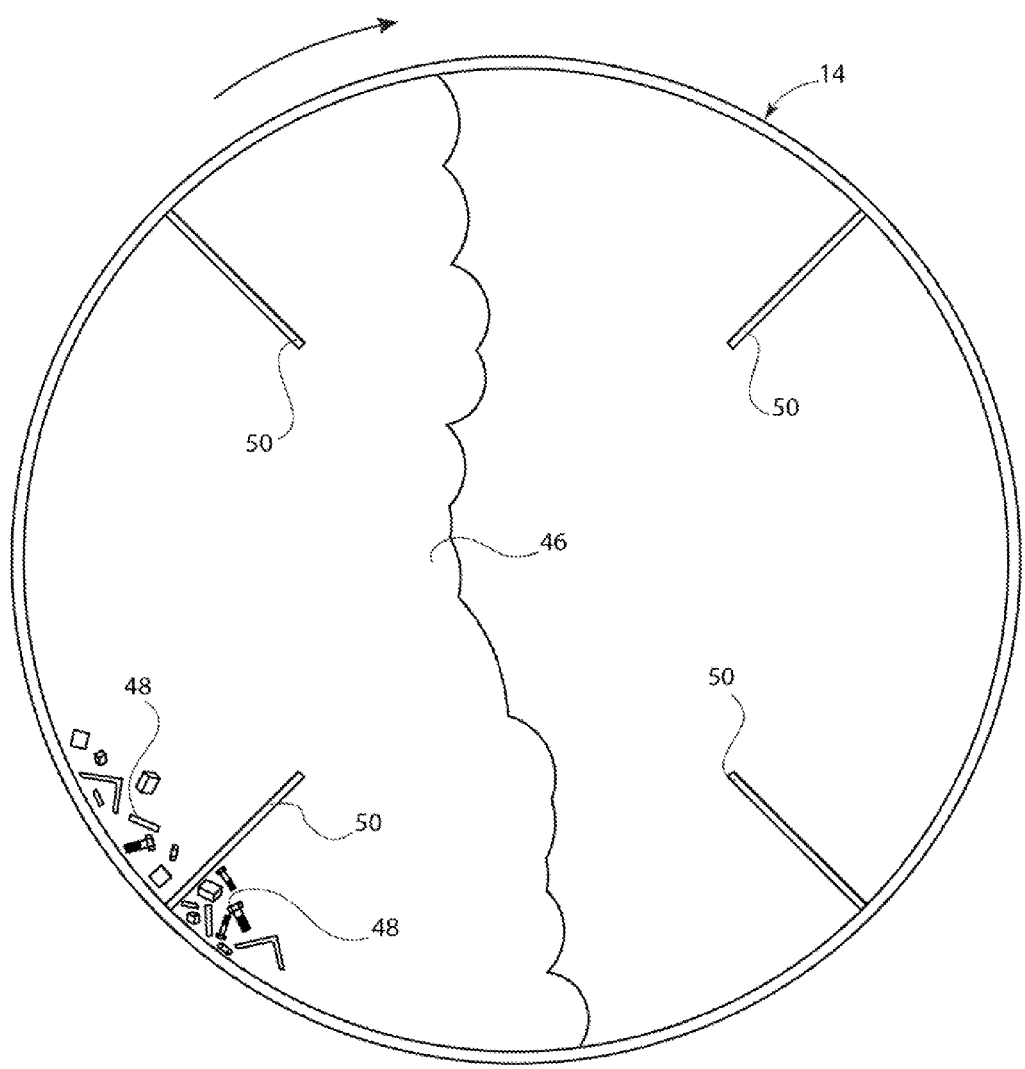
FIG. 2 is a schematic cross-sectional view of the autoclave of FIG. 1.

With reference to FIG. 2, in operation, the autoclave 14 is loaded with a load of absorbent sanitary products 46 and with a load of high-density tearing elements 48. The autoclave 14 is then sealably closed and pressurized by the contact steam. At the same time, the autoclave is heated by the non-contact steam. The autoclave, once heated and pressurized, is driven in rotation about the axis A. Inside the autoclave 14 there may be provided radial blades 50 projecting from the inner wall of the autoclave.

The high-density tearing elements 48 facilitate transfer of heat and destructuring of the absorbent sanitary products 46. The tearing elements 48 are made of a thermally conductive material, preferably metal material. The tearing elements 48 may be small and sharp objects such as for example stones or objects coming from metalwork such as screws, bolts, lengths of L-sectional steel, etc.

The tearing elements 48 absorb heat by conduction from the heated walls of the autoclave 14. During rotation of the autoclave 14 the mass of absorbent sanitary products 46 is entrained upwards by the walls of the autoclave and then drops towards the centre. Then, the tearing elements drop on top of the mass of absorbent sanitary products 46.

Given that the tearing elements 48 are heavy, they penetrate into the mass of absorbent sanitary products that has accumulated on the bottom of the autoclave 14 and reach the wall of the autoclave 14.

As the tearing elements 48 traverse the mass of absorbent sanitary products 46, they yield heat by conduction, convection, and radiation. In this way, the energy available on the wall of the autoclave 14 is effectively transferred within the mass of waste significantly increasing the effective surface of thermal exchange.

The tearing elements 48 are at the temperature of the wall of the autoclave or at a temperature close to the temperature of the wall of the autoclave, which is set at a value higher than the temperature for melting the enveloping plastic material of the absorbent sanitary products. As the tearing elements 48 pass through the mass of absorbent sanitary products 46, they weaken, tear, and form holes in the plastic envelopes thus destructuring the absorbent sanitary products and releasing the fibrous contents of the waste.

The amount in weight of tearing elements 48 necessary to obtain destructuring of the absorbent sanitary products 46 is between 0.25 and 5 times the dry weight of the load of products to be treated. The preferred amount is between 0.5 and 1.5 times the dry weight of the products 46.

In tests that have been conducted a successful destructuring of absorbent sanitary products has been obtained with steel bolts having a unit weight comprised between 0.25 and 1 kg, and with flat pieces of steel of the same weight.

The mass of tearing elements 48 in combination with the temperature and pressure inside the autoclave 14 enable a complete destructuring of the absorbent sanitary products inside the autoclave 14. In this way, there is avoided the need for a preliminary treatment of shredding of the products, which would expose the operators and the surrounding environment to evil odours and to the contaminating elements contained in the absorbent sanitary products.

Complete destructuring of the products during treatment in the autoclave enables drying and sterilization of the products in shorter times. After treatment in the autoclave a dried and sterile destructured mass is obtained, basically formed by plastic and cellulose fibres. Next, the dried and sterile destructured mass is passed through a sieve in which the plastic and the cellulose fibres are separated.

While the foregoing is directed to embodiments of the present invention, other and further embodiments of the invention may be devised without departing from the basic scope thereof, and the scope thereof is determined by the claims that follow.

The invention claimed is:

1. A process for treating used absorbent sanitary products, comprising the steps of:
   providing a rotary cylindrical autoclave having an inner surface and two ends;
   opening a hatch disposed on the cylindrical autoclave to enable access to the cylindrical autoclave, wherein the hatch may be sealably closed to enable pressurization of the cylindrical autoclave;
   loading the cylindrical autoclave with absorbent sanitary products;
   heating to a sterilization temperature and pressurizing the cylindrical autoclave and at the same time driving the cylindrical autoclave in rotation about a longitudinal axis thereof; and
   providing inside the cylindrical autoclave a plurality of high-density unsecured tearing elements designed to facilitate thermal and physical destructuring of the absorbent sanitary products.

2. The process according to claim 1, wherein the plurality of unsecured tearing elements are made of thermally conductive metal material.

3. The process according to claim 1, wherein the plurality of unsecured tearing elements has a weight that is 0.25 to 5 times a dry weight of the absorbent sanitary products.

4. The process according to claim 1, wherein the plurality of unsecured tearing elements has a weight that is 0.5 to 1.5 times a dry weight of the absorbent sanitary products.

5. The process according to claim 1, wherein the plurality of unsecured tearing elements are made of thermally conductive rock material.

6. The process according to claim 1, further comprising providing a plurality of longitudinally-extending blades designed to facilitate thermal and physical destructuring of the absorbent sanitary products.

* * * * *